(12) United States Patent
Morgan

(10) Patent No.: US 7,704,522 B2
(45) Date of Patent: Apr. 27, 2010

(54) TOPICAL MEDICAMENT

(76) Inventor: Clyde Morgan, 18448A High View Dr., Gardner, KS (US) 86030

( * ) Notice: Subject to any disclaimer, the term of this patent is extended or adjusted under 35 U.S.C. 154(b) by 861 days.

(21) Appl. No.: 11/220,138

(22) Filed: Sep. 6, 2005

(65) Prior Publication Data

US 2006/0051432 A1    Mar. 9, 2006

Related U.S. Application Data

(60) Provisional application No. 60/608,136, filed on Sep. 8, 2004.

(51) Int. Cl.
*A61F 13/00* (2006.01)
*A61L 15/16* (2006.01)

(52) U.S. Cl. ....................... 424/443; 424/444

(58) Field of Classification Search ............. 424/443, 424/444
See application file for complete search history.

(56) References Cited

U.S. PATENT DOCUMENTS

| | | |
|---|---|---|
| 4,455,146 A | 6/1984 | Noda et al. |
| 4,507,285 A | 3/1985 | Kühne |
| 4,623,346 A | 11/1986 | von Bittera et al. |
| 4,627,852 A | 12/1986 | von Bittera et al. |
| 4,661,104 A | 4/1987 | von Bittera et al. |
| 4,702,916 A | 10/1987 | Geria |
| 4,738,670 A | 4/1988 | von Bittera |
| 4,795,638 A | 1/1989 | Ayache et al. |
| 4,801,458 A | 1/1989 | Hidaka et al. |
| 4,844,902 A | 7/1989 | Grohe |
| 4,892,890 A | 1/1990 | Damani |
| 4,963,591 A | 10/1990 | Fourman et al. |
| 4,990,340 A | 2/1991 | Hidaka et al. |
| 5,145,675 A | 9/1992 | Won |
| 5,273,754 A | 12/1993 | Mann |
| 5,352,437 A | 10/1994 | Nakagawa et al. |
| 5,383,848 A | 1/1995 | Hillman et al. |
| 5,429,590 A | 7/1995 | Saito et al. |
| 5,468,492 A | 11/1995 | Szaloki et al. |
| 5,505,958 A | 4/1996 | Bello et al. |
| 5,597,849 A | 1/1997 | McGinity et al. |
| 5,622,993 A | 4/1997 | McGinity et al. |
| 5,626,856 A | 5/1997 | Berndt |
| 5,665,386 A | 9/1997 | Benet et al. |
| 5,716,621 A | 2/1998 | Bello et al. |
| 5,716,625 A | 2/1998 | Hahn et al. |
| 5,716,928 A | 2/1998 | Benet et al. |
| 5,770,220 A | 6/1998 | Meconi et al. |
| 5,780,047 A | 7/1998 | Kamiya et al. |
| 5,804,173 A | 9/1998 | Hutchins et al. |
| 5,804,203 A | 9/1998 | Hahn et al. |
| 5,830,447 A | 11/1998 | Hutchins et al. |
| 5,855,922 A | 1/1999 | Danner et al. |
| 5,858,330 A | 1/1999 | Boltri et al. |
| 5,863,527 A | 1/1999 | Hutchins et al. |
| 5,866,143 A | 2/1999 | Elkhoury |
| 5,882,663 A | 3/1999 | Koeniger et al. |
| 5,891,463 A | 4/1999 | Bello et al. |
| 5,916,548 A | 6/1999 | Hutchins et al. |
| 5,916,566 A | 6/1999 | Benet et al. |
| 5,942,233 A | 8/1999 | Chang |
| 5,955,067 A | 9/1999 | Oge et al. |
| 5,980,925 A | 11/1999 | Jampani et al. |
| 6,103,266 A | 8/2000 | Tapolsky et al. |
| 6,121,234 A | 9/2000 | Benet et al. |
| 6,139,850 A | 10/2000 | Hahn et al. |
| 6,139,876 A | 10/2000 | Kolta |
| 6,143,317 A | 11/2000 | Himmelsbach et al. |
| 6,174,891 B1 | 1/2001 | Nagase et al. |
| 6,239,180 B1 | 5/2001 | Robbins |
| 6,252,003 B1 | 6/2001 | Kuwahara et al. |
| 6,258,857 B1 | 7/2001 | Iijima et al. |
| 6,270,783 B1 | 8/2001 | Slavtcheff et al. |
| 6,277,398 B1 | 8/2001 | Caruso |
| 6,277,401 B1 | 8/2001 | Bello et al. |
| 6,284,234 B1 | 9/2001 | Niemiec et al. |
| 6,299,885 B1 | 10/2001 | Yamasaki et al. |
| 6,306,412 B1 | 10/2001 | Crotty et al. |
| 6,316,461 B1 | 11/2001 | Nagase et al. |

(Continued)

OTHER PUBLICATIONS

Ralph Moss, PhD.: The Moss Reports #64, Moss Reports on Spirulina (#64), 4 pages, www.annieappleseedproject.org/mosreponspir.html.
"What is Spirulina," 3 pages, www.naturalways.com/spirul1.htm.
"Aerobic 07 Stabilized Oxygen Water Purification Drops," 4 pages, http://www.baproducts.com/aerobic.htm.
Bicarbonates definition, 1 page (no other information available).
"Cellular Metabolism and Fermentation," 8 pages, http://www.emc.maricopa.edu/faculty/farabee/BIOBK/BioBookGlyc.html.
"Cellular Respiration," 5 pages, http://users.rcn.com/jkimball.ma.ultranet/BiologyPages/C/CellularRespiration.html.
TerBeek, Kenneth J., "Explosion with Sodium Chlorite," Chemical & Engineering News, Mar. 22, 1993, vol. 71, No. 12, p. 4.
Youn, Brian A., MD., "Oxygen and its Role in Wound Healing," Geisinger Medical Center, 5 pages.

(Continued)

*Primary Examiner*—Sreeni Padmanabhan
*Assistant Examiner*—Renee Claytor
(74) *Attorney, Agent, or Firm*—Hovey Williams LLP

(57) ABSTRACT

New topical medicaments are provided. The medicaments comprise menthol and camphor, preferably provided as part of a base gel, supplemented with potassium and a source of oxygen. The most preferred base gel is sold under the name SOMBRA, while the most preferred source of oxygen is a chlorite (e.g., sodium chlorite) and/or spirulina. The medicaments provide high metabolic activities and sustain those activities over prolonged periods of time, thus being useful for treating a large variety of ailments, including diabetic neuropathy, post hepatic neuralgia, scleroderma, psoriasis, strain, spasticity, headaches, neuropathy secondary to drugs, peripheral neuropathy, leg pain, muscle cramps, muscle aches and pains, bruise, sinusitis, sprain, arthritis, joint pain (arthralgia), and edema.

8 Claims, 4 Drawing Sheets

U.S. PATENT DOCUMENTS

| | | |
|---|---|---|
| 6,328,982 B1 | 12/2001 | Shiroyama et al. |
| 6,335,023 B1 | 1/2002 | Yu et al. |
| 6,348,218 B1 | 2/2002 | Hed et al. |
| 6,359,032 B1 | 3/2002 | Kuwahara et al. |
| 6,409,997 B1 | 6/2002 | Castro |
| 6,419,913 B1 | 7/2002 | Niemiec et al. |
| 6,432,415 B1 | 8/2002 | Osborne et al. |
| 6,433,061 B1 | 8/2002 | Marchant et al. |
| 6,440,987 B1 | 8/2002 | Nagase et al. |
| 6,495,498 B2 | 12/2002 | Niemiec et al. |
| 6,524,594 B1 | 2/2003 | Santora et al. |
| 6,555,130 B2 | 4/2003 | Wüstling et al. |
| 6,559,168 B2 | 5/2003 | Marfat et al. |
| 6,576,623 B1 | 6/2003 | Nakanishi et al. |
| 6,579,543 B1 | 6/2003 | McClung |
| 6,582,724 B2 | 6/2003 | Hsu et al. |
| 6,586,000 B2 | 7/2003 | Luo et al. |
| 6,592,896 B2 | 7/2003 | Rosenbloom |
| 6,596,313 B2 | 7/2003 | Rosenbloom |
| 6,623,756 B1 | 9/2003 | Wilber et al. |
| 6,635,702 B1 | 10/2003 | Schmucker-Castner et al. |
| 6,638,981 B2 | 10/2003 | Williams et al. |
| 6,645,506 B1 | 11/2003 | Farmer |
| 6,645,520 B2 | 11/2003 | Hsu et al. |
| 6,646,012 B2 | 11/2003 | Choi et al. |
| 6,649,633 B2 | 11/2003 | Chambers et al. |
| 6,653,352 B2 | 11/2003 | Barr et al. |
| 2002/0114849 A1 | 8/2002 | Camper et al. |

OTHER PUBLICATIONS

Ali, Majid MD., "Seven Aspects of Oxygen & Oxidation," 3 pages, http://majidali.com/seven.htm.
Two paragraph description of Spirulina, 1 page, http://www.spirulinasource.com/earthfoodchla.html.
Six paragraph description of Spirulina Pacifica, 1 page (no other information available).
"Spirulina: Huge Health Benefits," 8 pages, http://www.relfe.com/spirulina_heath_benefits.html,www.relfe.com//spirulina_health_benefits%20_2.html,www.relfe.com//spirulina_health_benefits%20_3.html.
Hofbauer, Gess B. et al., "The Cellular Oxygen Tension Regulates Expression of the Endoplasmic Oxidoreductase ER01-Lalpha," Eur. J. Biochem., 270, 2228-2235 (2003), Instit fur Physiologie der Universitat Regensburg, Germany, http://content.febsjournal.org/cgi/content/full/270/10/2228.
Stabilized Oxygen Supplement from WaterOz, 3 pages, http://wateroz.jeffotto.com/products/oxygen.htm.
ATP—The Universal Energy Carrier in the Living Cell, Boyer et al., 10 pages, http://www.eyesight.org/Research/Research-ATP/research-atp.html.
Deficiencies Caused by IBD, 3 pages (no other information available).
Neuropathy, ReBuilder Materials, 9 pages (no other information available).
Klabunde, Richard E. PhD., "Metabolic Mechanisms of Vasodilation," Revised Aug. 29, 2005, 3 pages, http://www.cvphysiology.com/Blood%20Flow/BF008.htm.
Abbott, G.W. et al., "MiRP2 Forms Potassium Channels in Skeletal Muscle with Kv3.4 and is Associated with Periodic Paralysis," Cell, 104:217-231, Jan. 26, 2001 http://www.ncbi.nlm.nih.gov/entrez/query.fcgi?cmd=Retrieve&db=PubMed&Lis_uids=112 . . . .
Misner, Bill, PhD., "Muscle Cramps: Dealing with Heat Stress During Endurance Exercise," 6 pages, http://www.fit-zone.com/library/E/Endurance_Training/cramps.html.
Muscle Spasms 3 pages (no other information available).
Muscles, Aug. 26, 2004, 12 pages, http://users.erols.com/jkimball.ma.ultranet/BiologyPages/M/Muscles.html.
Na+/K+(Sodium/Potassium) Pump, 1 page (no other information available).
Nerve Impulses, Updated Apr. 17, 2004, 14 pages, http://www.biologymad.com/NervousSystem/nerveimpulses.htm.
Neuropathy and Diabetes, ReBuilder Materials, 4 pages (no other information available).
Potassium, 18 pages, http://www.ithyroid.com/potassium.htm.
Haas, Elson M. MD., "Potassium," 5 pages, http:www.healthy.net/scr/article.asp?ID=2063.
Dr. T. Dixon, Potassium Balance, 12 pages, http://www.uhmc.sunysb.edu/internalmed/nephro/webpages/Part_D.htm.
"Potassium is a Mineral that is Required in Significant Amounts for Human Health. Potassium Balances Sodium in the Body to Regulate Hydration." Diagnose-Me: Condition: Potassium Need, 2 pages, http://www.diagnose-me.com/cond/C424831.html.
Potassium, 2 pages, http:www.elementalresearchllc.com/potassium.htm.
"Potassium is required for , . . . " 13 brief paragraphs regarding potassium, 2 pages (no other information available).
Weber, Charles MS., "Potassium Nutritional Losses and Recommended Daily Requirement," Updated Jan. 2005, 13 pages, http://members.tripod.com/~charles_W/arthritis8.html.
Potassium with Magnesium Citrate, 3 pages, http://wwwo.organicfood.co.uk/vns/potassium-magcit.html.
Potassium, The Llnus Pauling Institute, 9 pages, http://lpi.oregonstate.edu/inforcenter/minerals/potassium/.
Pyruvate Kinase, 10 pages, http:www.worthington-biochem.com/PKL/default.html.
Transport In and Out of Cells, 12 pages, http://www.emc.maricopa.edu/faculty/farabee/BIOBK/BioBooktransp.html.
Joint Inflammation, 5 pages (no other information available).
Contusion; Hematoma, 2 pages (no other information available).
Cramps—muscle, 2 pages (no other information available).
Nerve damage—diabetic, 2 pages (no other information available).
Edema; Anasarca, 3 pages (no other information available).
Stiffness in a joint; Pain—joints; Arthralgia, 3 pages (no other information available).
Pain—leg; Aches—leg; Cramps—leg, 3 pages (no other information available).
Muscle pain; Myalgia; Pain—muscles, 3 pages (no other information available).
Peripheral neuritis; Neuropathy—peripheral; Neuritis—peripheral, 5 pages (no other information available).
Neuropathy secondary to drugs . . . , 2 pages (no other information available).
Nerve pain; postherpetic neuralgia, 4 pages (no other information available).
Plaque psoriasis, 3 pages (no other information available).
Acute sinusitis; Sinus infection; Sinusitis—acute, 4 pages (no other information available).
Spasticity is a condition described by stiff or rigid muscles . . . , 2 pages (no other information available).
Joint Sprain, 2 pages (no other information available).
Pulled Muscle, 1 page (no other information available).
Muscle contraction headache; Benign headache; Headache—tension, 3 pages (no other information available).
"Below is a list of symptoms and diseases that have positive results . . . ," Definitions taken from Medline Plus Medical Encyclopedia, 1 page (no other information available).
Atkins, David. L., "A Tutorial in Basic Neurobiology," 61 pages, http://sky.bsd.uchicago.edu/Icy_ref/synap/resting.html.
Sombra, Natural Pain Relieving Gel, 1 page, http:www.sombrausa.com/somingpg.htm.
Earthrise Spirulina Dietary Supplement Capsules (Photograph of Bottle), 4 pages.
Nature's Way Potassium Chelate Capsules (Photograph of Bottle), 3 pages.
CC Medical Devices, Inc. My Alivio Cream (Photograph of Bottle), 2 pages.
http://www.patentstorm.us/patents/6337327—description.html, Patent Storm, "Pharmaceutical Compositions Comprising an Aldose Reductase Inhibitor and an Ace Inhibitor," U.S. Patent No. 6,337,327, Cameron et al., Jan. 8, 2002.
Office Action dated Oct. 28, 2009 in U.S. Appl. No. 11/866,573 (35085-CIP).

TOPICAL MEDICAMENT

RELATED APPLICATIONS

This application claims the priority benefit of U.S. Provisional Patent Application No. 60/608,136, filed Sep. 8, 2004, incorporated by reference herein.

BACKGROUND OF THE INVENTION

1. Field of the Invention

The present invention is broadly concerned with improved topical medicaments in forms of creams or lotions which are useful in the treatment of a variety of conditions that are ameliorated by increased cell metabolism, circulation, and nerve function. More particularly, the invention is concerned with such medicaments having a gel base with menthol and camphor, and supplemented with potassium and an oxygen source such as an alkali metal chlorite.

2. Description of the Prior Art

A variety of topically applied creams and lotions have been developed in the past for treatment of conditions such as arthritis and muscle pains. One such product is commercialized under the designation SOMBRA. This product contains 3% menthol and 3% camphor, in a gel base, and is used for the temporary relief of minor aches and pains of muscles and joints associated with simple backaches, arthritis, strains, bruises, and sprains.

However, many prior art creams and lotions do not adequately treat these conditions in most people. Furthermore, even those that are successful do not sustain metabolic activity for extended periods of time, thus making any relief experienced rather temporary. There is a need for new treatments that provide relief for a wide variety of conditions and for extended periods of time.

SUMMARY OF THE INVENTION

The present invention overcomes these problems by broadly providing novel topical medicaments having improved metabolic activity.

In more detail, the inventive medicaments comprise menthol, camphor, potassium, and a source of oxygen. The menthol and camphor can be individually added to the composition, or they can be added via a base composition including menthol and camphor. One preferred base composition is a gel sold under the name SOMBRA. Regardless of the delivery source, the menthol is preferably present in the medicament at a level of at least about 0.5% by weight, more preferably from about 2-20% by weight, and even more preferably from about 2-4% by weight, based upon the total weight of the medicament taken as 100% by weight. Furthermore, the camphor is preferably present in the medicament at a level of at least about 0.5% by weight, more preferably from about 2-20% by weight, and even more preferably from about 2-4% by weight, based upon the total weight of the medicament taken as 100% by weight.

The potassium is preferably provided in powder form, and it can be obtained from dietary supplements, for example. One preferred source of potassium is Potassium Chelate (99 mg potency) sold by Nature's Way. Potassium Chelate is provided in the form of a capsule including powder potassium and minor amounts of ground millet. The capsule can simply be opened, and the powder from the capsule used in the present invention. Potassium is preferably present in the medicament at a level of at least about 0.02% by weight, more preferably from about 0.04-0.5% by weight, and even more preferably from about 0.09-0.2% by weight, based upon the total weight of the medicament taken as 100% by weight. When Potassium Chelate or a similar product is used, preferably from about 1-20 capsules, more preferably from about 1-15 capsules, and even more preferably from about 8-13 capsules are used.

The source of oxygen can be any source that is capable of delivering the appropriate levels of oxygen to the medicament. Suitable oxygen sources include those selected from the group consisting of chlorites (and preferably alkali metal chlorites such sodium chlorite and magnesium chlorite), spirulina, and mixtures of the foregoing. The most preferred oxygen source is sold under the name AEROBIC 07, which contains deionized water, sodium chlorite, carbonates, and bicarbonates.

The oxygen source is preferably present in the medicament in sufficient quantities to provide oxygen levels of at least about 0.016% by weight, more preferably from about 0.10-0.85% by weight, and even more preferably from about 0.17-0.25% by weight, based upon the total weight of the medicament taken as 100% by weight. When AEROBIC 07 or a similar product is used, it is preferably added at levels of from about 1-13 drops, more preferably from about 1-10 drops, and even more preferably about 4 drops.

In one alternative embodiment, the medicament also includes a source of chlorine ions. If sodium chlorite is used as the source of oxygen, it will also functions as a source of chlorine ions. Other suitable sources of chlorine ions include any chlorite (e.g., sodium hypochlorite) such as those found in commercially available bleaching agents (e.g., CLOROX, CALIBEX). In these embodiments, the source of chlorine is included in sufficient quantities to provide chlorine ion levels of from about 0.10-10% by weight, and more preferably from about 0.16-0.85% by weight, based upon the total weight of the medicament taken as 100% by weight.

The inventive medicaments can also include a number of optional ingredients, depending upon the final use. Some suitable ingredients include those selected from the group consisting of aloe vera extract, capsaicin, carbomer, decyl plyglucose, deionized water, grapefruit seed extract, green tea extract, orange peel extract, queen of the prairie extract, rose water, silica, sodium hydroxymethyl glycinate, vegetable glycerin, witch hazel, yucca extract, carbonates, bicarbonates, and mixtures of the foregoing. The preferred quantities of these ingredients are set forth in Table 1. These ingredients can be added individually or in a group as part of another composition (e.g., in a base composition such as SOMBRA).

TABLE 1

| INGREDIENT | BROAD RANGE[A] | MORE PREFERRED RANGE[A] |
|---|---|---|
| *Aloe Vera* Extract | 0.10-50% | 0.25-1.75% |
| Capsaicin | 0.001-10% | 0.25-1.75% |
| Carbomer | 1.35-30% | 2.75-19.25% |
| Decyl Plyglucose | 0.1-9% | 0.5-3.5% |
| Deionized Water | 20-90% | 76.5-90% |
| Grapefruit Seed Extract | 0.001-5% | 0.25-1.75% |
| Green Tea Extract | 0.05-10% | 0.5-3.5% |
| Orange Peel Extract | 0.001-5% | 0.25-1.75% |
| Queen of the Prairie Extract | 0.25-20% | 2.25-15.75% |
| Rose Water | 0.2-7% | 0.5-3.5% |
| Silica | 0.03-20% | 1-7% |
| Sodium Hydroxymethyl Glycinate | 0.05-25% | 1.25-8.75% |
| Vegetable Glycerin | 0.09-50% | 1.75-12.25% |
| Witch Hazel | 0.02-15% | 1-7% |
| Yucca Extract | 0.015-30% | 0.5-3.5% |
| Carbonates | 0.025-3.5% | 0.25-1.75% |
| Bicarbonates | 0.025-3.5% | 0.25-1.75% |

[A]The percentages by weight are based upon the total weight of the topical medicament taken as 100% by weight.

The inventive medicaments are formed by simply mixing the above ingredients together, preferably in some type of carrier. If SOMBRA is used, then the carrier is provided by that product.

In a particularly preferred preparation method, a precursor composition containing the camphor and menthol is provided. The precursor composition should comprise:

from about 1-10% by weight menthol, preferably from about 1-5% menthol, and even more preferably about 3% by weight menthol; and from about 1-10% by weight camphor, preferably from about 1-5% camphor, and even more preferably about 3% by weight camphor, based upon the total weight of the medicament taken as 100% by weight.

The precursor composition can also include some or all of the optional ingredients discussed above.

A quantity of the precursor composition is added to a container, along with a portion of the potassium. Further respective quantities of the precursor composition and potassium are then added in alternating steps until the desired quantity as been obtained. The precursor composition and potassium within the container are preferably then mixed until substantially homogeneous (e.g., from about 1-3 minutes, and preferably about 2 minutes). Mixing can be carried out by hand or mechanical mixing means (e.g., mixer, shearing in industrial equipment). The source of oxygen is then added to the resulting mixture and further mixing is carried out. Any optional ingredients that were not already added can then be added to the mixture to yield the final medicament.

The inventive topical medicament is used to treat a portion of the body (human or animal) afflicted with an ailment by simply contacting the medicament with the afflicted portion of the body. The medicament is then preferably rubbed into the skin until it is no longer visible. It will be appreciated that the medicament can be used to treat numerous conditions, including diabetic neuropathy, post hepatic neuralgia, scleroderma, psoriasis, strain, spasticity, headaches, neuropathy secondary to drugs, peripheral neuropathy, leg pain, muscle cramps, muscle aches and pains, bruise, sinusitis, sprain, arthritis, joint pain (arthralgia), and edema.

The inventive medicament offers a particularly significant advantage in that it achieves high metabolic activity and maintains that activity over extended periods of time. "Metabolic activity" as used herein refers to energy (in mV) that is created by the potassium ions in the medicament. That energy is then transferred to the patient at the medicament location on the skin. Though not wishing to be bound by theory, it is believed that the energy excites and thus opens the sodium-potassium pumps in the cells. This stimulates the nervous system and better allows active ingredients to enter the cells.

Metabolic activity is determined by mixing 1 g of a medicament with 0.1 g of a commercially available electrolyte material (e.g., one sold under the name ORAL REHYDRATION SALTS, available from Jianas Bros. Packaging Co.). The mixture is then placed onto an electrogel pad, which is "sandwiched" between two ECG patches connected to a voltmeter. Readings in mV are taken over regular intervals (e.g., 5-minute intervals).

When using the medicaments of the invention, a peak (i.e., highest or maximum) metabolic activity of at least about 2.5 mV, preferably at least about 4 mV, and more preferably from about 4-20 mV is achieved. This peak is preferably achieved within about 30 minutes, and more preferably within about 15 minutes, of application to the afflicted area.

The inventive medicaments also possess the property of having a retained metabolic activity of at least about 20%, preferably at least about 30%, and even more preferably from about 50-100% over a 45-minute time period. Furthermore, the inventive medicaments possess the property of having a retained metabolic activity of at least about 5%, preferably at least about 20%, and even more preferably from about 25-100% over an 8-hour time period. As used herein, "retained metabolic activity" is determined as follows:

$$\text{Retained Metabolic Activity} = \left[\frac{\text{metabolic activity after 45 minutes or 8 hours}}{\text{peak metabolic activity}}\right] \times 100$$

BRIEF DESCRIPTION OF THE DRAWINGS

FIG. 1$b$ is a graph depicting the metabolic activity of another prior art product over a 45-minute time period;

FIG. 1$c$ is a graph depicting the metabolic activity of the inventive medicament over a 45-minute time period; and FIG. 1$d$ is a graph depicting the metabolic activity of the inventive medicament over an 8-hour time period.

DETAILED DESCRIPTION OF THE PREFERRED EMBODIMENTS

EXAMPLES

Figure 1A:
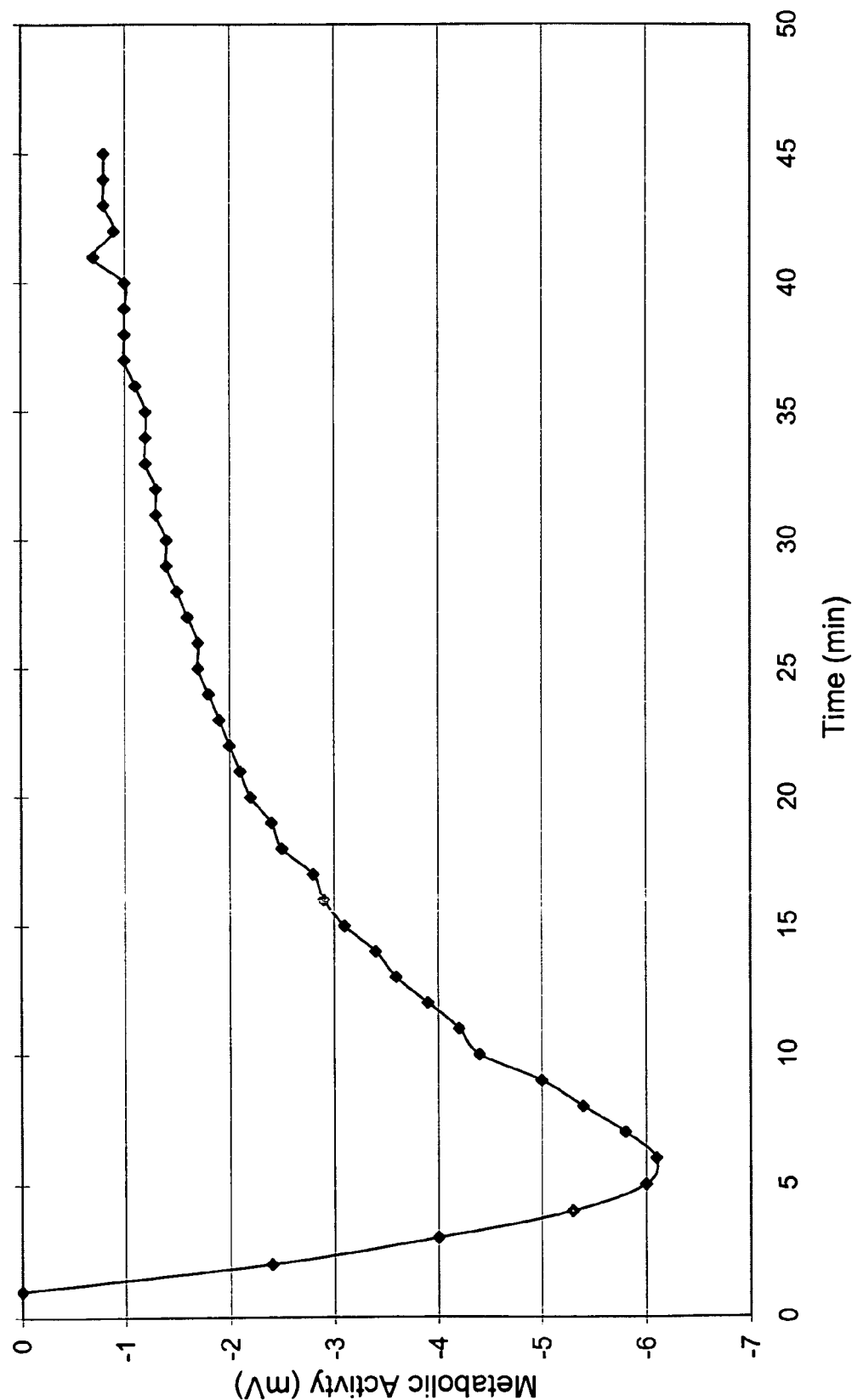
FIG. 1$a$ is a graph depicting the metabolic activity of a prior art product over a 45-minute time period.

The following examples set forth preferred methods in accordance with the invention. It is to be understood, however, that these examples are provided by way of illustration and nothing therein should be taken as a limitation upon the overall scope of the invention.

Example 1

Preparation of Topical Medicament

A 1-gallon plastic jug was tared on a Sunbeam Model SP5 top balance (no shield, small pan balance). The jug was then charged with 5.7 oz of SOMBRA Natural Pain Relieving Gel (available from Sombra Inc., Albuquerque, N.Mex.).

Thirteen potassium amino acid chelate capsules (99 mg potassium with millet filler; available from Nature's Way, Springville, Utah) were emptied three at a time. The filled capsule weight was 0.78 g, the emptied powder weight was 0.67 g, and the empty capsule weight was 0.67 g (n=1). The level of elemental potassium in the capsule was not given on the label.

The powder emptied from the capsules was then added to the SOMBRA in the plastic jug as follows:

(1) The jug was charged with SOMBRA to a weight of 12.1 oz., and the powder from three empty capsules was added;

(2) The jug was charged with SOMBRA to a weight of 1 lb. 6.1 oz., and the powder from three empty capsules was added;

(3) The jug was charged with SOMBRA to a weight of 2 lb. 3.9 oz., and the powder from the remaining empty capsules was added; and (4) The jug was charged to a final weight of 3 lb. 1 oz. with SOMBRA.

A cap was placed on the jug, and the jug was shaken by hand for about 2 minutes to substantially evenly distribute the powder. The gel did not adhere to the plastic jug after the potassium amino acid chelate was added.

AEROBIC 07 (a dietary supplement including deionized water, sodium chlorite, carbonates, and bicarbonates; available from Aerobic Live, Phoenix, Ariz.) was used as a stabilized source of oxygen. Thirteen drops of the Aerobic 07 were added to the plastic jug containing the SOMBRA-potassium amino acid chelate mixture. The jug was again capped and shaken by hand for about 2 minutes to yield the final topical medicament. The final medicament was more viscous than the SOMBRA gel. When comparing a quantity of each, the compounded medicament did not separate or flow as compared to the SOMBRA gel, which showed some physical separation.

Example 2

Treatment of Patient A

1. Patient History

The topical medicament prepared in Example 1 was used to treat a patient (hereinafter referred to as "Patient A"). Patient A was a Caucasian female in her 60s, and she was 5'7" and approximately 220 lb. Patient A exhibited neuropathy of the legs and feet, with the left leg being worse than the right. Patient A's big toe on her right foot and second toe on her left foot were amputated within the preceding 3 years due to diabetes. She had received angioplasty about 9 months prior, and the angioplasty improved blood flow to her lower extremities.

Both legs below the knees presented open sores about half-way between the knee caps and ankles. The sores were worse on the right leg than the left. She had used Bactroban and Betadine to treat the topical sores for infection.

Patient A also had an ulcer on the bottom of her right foot. She had begun a second, 2-3 week treatment course of Regranex, applying at bedtime. Previous use of Regranex had worked, but the ulcer recurred, so she then had surgery. She began to use Etherex, which she stated is a generic medicine for Regranex and Bactroban. Her daily medications are shown in Table A-B.

TABLE A

| PRESCRIPTION MEDICATION | DOSAGE |
| --- | --- |
| Lisinopril 20/12.5 | 2 p.o. qd |
| Atenolol 50 mg | 1½ p.o. qd |
| Lipitor 40 mg | 1 p.o. qd |
| Insulin | 40 u of N and 10 u of Humalog in morning; 40 u of N and 10 u of Humalog before dinner |
| Paroxitine (Paxil) 40 mg | p.o. qd |
| Levothyroxine 0.3 mg | p.o. qd |
| Calcitrol 0.25 µg | 1 p.o. bid |
| Niaspan 500 mg | 1 p.o. q evening |
| Plavix 75 mg | 1 p.o. qd |
| Furosemide 80 mg | p.o. 1 daily |
| Diovan 320 mg | 1 daily |
| Procrit | 1 injection q 2 weeks until no longer needed |
| Dynacirc 5 mg | 1 p.o. daily |

TABLE B

| VITAMINS AND OVER-THE-COUNTER MEDICATIONS | DOSAGE |
| --- | --- |
| Multivitamin | 1 p.o. daily |
| Prilosec | 1 p.o. daily |
| Low-Dose Aspirin | 1 every evening |
| Iron | 2 "pills" each day for anemia |

Patient A also reported using Walitin (generic for Claritin) and Nasonex as needed for allergies.

2. Treatment with Inventive Topical Medicament

The ambient temperature during treatment ranged from 74-78° F. according to measurements from four different Stress Thermometers used "as is" (Dr. Lowenstein's Model SC911 accuracy +/−1.8° F., 10 ft. lead with fast temperature sensor).

Patient A was recumbent on a treatment table with a triangular pillow positioned behind both knees so that the knees were bent upward to rise above the ankles. A temperature probe was strapped on each upper ventral thigh and on the inside of each ankle. The probes were covered, and no medicament was applied to the probes. Equilibration time was approximately 10 minutes after the patient reclined in the prone position. After equilibration time was reached, the temperatures were recorded as shown in Table C.

TABLE C

| PROBE LOCATION | TEMPERATURE |
| --- | --- |
| right thigh | 90.0° F. |
| left ankle | 86.7° F. |
| right thigh | 92.3° F. |
| right ankle | 90.1° F. |

The inventive medicament was applied to the top and bottom of each thigh and later (as shown in Table D) to the top and bottom of each calf, ankle, and foot. The product was massaged into the skin until nearly invisible to the eye. The dosage level was 0.3 oz. on each thigh and each ankle for a total per leg dosage of 0.6 oz.

Temperature readings were taken at intervals, beginning 5 minutes after application to Patient A's legs. These readings are set forth in Table D.

TABLE D

| TIME | LOCATION | TEMPERATURE (° F.) |
| --- | --- | --- |
| 5 minutes[4] | left thigh | 90.5 |
| | left ankle | 86.9 |
| | right thigh | 92.3 |
| | right ankle | 90.9 |
| Note - Patient A reported feeling heat at 5 minutes. | | |
| 7 minutes | left thigh | 90.9 |
| | left ankle | 86.9 |
| | right thigh | 92.3 |
| | right ankle | 90.9 |
| 10 minutes | left thigh | 91.5 |
| | left ankle | 86.9 |
| | right thigh | 92.5 |
| | right ankle | 91.2 |
| Note - Patient A reported heat at same level as at 5 minutes. | | |
| 15 minutes | left thigh | 91.4 |
| | left ankle | 87.1 |
| | right thigh | 92.1 |
| | right ankle | 90.7 |
| Note - Patient A reported feeling a warm sensation. There was sweat behind the left knee. Medicament was applied to left ankle at 17 minutes. A paper towel was placed on the triangular pillow. | | |
| 20 minutes | left thigh | 91.2 |
| | left ankle | 86.7 |
| | right thigh | 91.9 |
| | right ankle | 90.1 |
| 25 minutes | left thigh | 91.2 |
| | left ankle | 86.5 |
| | right thigh | 91.8 |
| | right ankle | 90.3 |

TABLE D-continued

| TIME | LOCATION | TEMPERATURE (° F.) |
|---|---|---|
| 30 minutes | left thigh | 91.2 |
|  | left ankle | 86.9 |
|  | right thigh | 91.6 |
|  | right ankle | 90.3 |
| 35 minutes | left thigh | 91.6 |
|  | left ankle | 86.9 |
|  | right thigh | 91.8 |
|  | right ankle | 90.5 |
| Note - Medicament was applied to right ankle at 35 minutes. | | |
| 40 minutes | left thigh | 91.4 |
|  | left ankle | 86.9 |
|  | right thigh | 90.3 |
|  | right ankle | 90.5 |
| 45 minutes | left thigh | 91.2 |
|  | left ankle | 86.9 |
|  | right thigh | 88.7 |
|  | right ankle | 90.1 |
| 50 minutes | left thigh | 91.2 |
|  | left ankle | 86.4 |
|  | right thigh | 89.2 |
|  | right ankle | 90.5 |
| 55 minutes | left thigh | 91.2 |
|  | left ankle | 87.3 |
|  | right thigh | 89.4 |
|  | right ankle | 90.1 |
| Note - At 57 minutes, Patient A reported a cool feeling from above the ankle to the heel. | | |
| 60 minutes | left thigh | 91.4 |
|  | left ankle | 87.3 |
|  | right thigh | 90.0 |
|  | right ankle | 90.1 |
| 65 minutes | left thigh | 91.2 |
|  | left ankle | 87.4 |
|  | right thigh | 90.5 |
|  | right ankle | 90.5 |
| 70 minutes | left thigh | 91.0 |
|  | left ankle | 87.3 |
|  | right thigh | 90.7 |
|  | right ankle | 90.1 |

[A]Five minutes after application to left calf and lower thigh (0 time).

Patient A rose from the table at 78 minutes, and the thigh probes were removed. Patient A held the readout portion of the thermometers in her hand while the probes were still attached to the ankles to allow her to walk to the restroom and take a further readout of her ankles after 5 minutes elapsed. However, at 82 minutes the left ankle probe came loose so no reading was taken. The right ankle probe gave a reading of 81.1° F. at 82 minutes. Patient A reported that her left side (neuropathic side) felt soothed.

Example 3

Treatment of Patient B

1. Patient History

The topical medicament prepared in Example 1 was used to treat a second patient (hereinafter referred to as "Patient B"). Patient B was a 60-year old, 5'7", Caucasian female. She was a non-insulin dependent diabetic and had sensory neuropathy that was worse in her right leg. She did not have any visible wounds. Her daily oral medications were Glucophage (1 in the evening), Toprol, Diovan, and Lipitor (1 in the evening).

2. Treatment with Inventive Topical Medicament

The ambient temperature during treatment ranged from 74-75° F. according to measurements from the four different Stress Thermometers as described in Part 2 of Example 2. The probes were applied as described in Part 2 of Example 2. The initial readings are shown in Table E.

TABLE E

| PROBE LOCATION | TEMPERATURE[A] | TEMPERATURE[C] |
|---|---|---|
| left thigh | 88.7° F. | 89.1° F. |
| left ankle | 83.8° F. | 83.8° F. |
| right thigh | 79.0° F.[B] | 90.7° F. |
| right ankle | 86.5° F. | 86.5° F. |

[A]Temperature prior to medicament application.
[B]The probe came loose from the right thigh, thus resulting in the 79° F. reading.
[C]Temperature at 4 minutes after temperature reading in middle column.

Temperature readings were taken as described in Part 2 of Example 2. These readings and the times of medicament application to Patient B's legs are set forth in Table F.

TABLE F

| TIME | LOCATION | TEMPERATURE (° F.) |
|---|---|---|
| 5 minutes[A] | left thigh | 90.5 |
|  | left ankle | 81.5 |
|  | right thigh | 91.6 |
|  | right ankle | 86.2 |
| Note - The inventive medicament was applied to the entire left leg at 5 minutes. At 7 minutes, Patient B reported that her left leg was cool. | | |
| 10 minutes | left thigh | 90.5 |
|  | left ankle | 81.5 |
|  | right thigh | 91.9 |
|  | right ankle | 85.8 |
| 15 minutes | left thigh | 90.7 |
|  | left ankle | 81.5 |
|  | right thigh | 92.3 |
|  | right ankle | 85.8 |
| 20 minutes | left thigh | 90.9 |
|  | left ankle | 81.1 |
|  | right thigh | 92.1 |
|  | right ankle | 85.5 |
| Note - Patient B reported feeling a stinging sensation behind her left knee, and that the toes on her left foot felt strange. | | |
| 25 minutes | left thigh | 91.0 |
|  | left ankle | 81.1 |
|  | right thigh | 92.3 |
|  | right ankle | 84.7 |
| Note - Patient B reported that she still felt a stinging sensation behind her left knee. | | |
| 30 minutes | left thigh | 91.6 |
|  | left ankle | 81.1 |
|  | right thigh | 92.8 |
|  | right ankle | 84.7 |
| 35 minutes | left thigh | 91.6 |
|  | left ankle | 81.1 |
|  | right thigh | 93.0 |
|  | right ankle | 82.9 |
| Note - The inventive medicament was applied to the entire right leg at 35 minutes. | | |
| 40 minutes | left thigh | 91.9 |
|  | left ankle | 81.0 |
|  | right thigh | 93.6 |
|  | right ankle | 83.3 |
| 45 minutes | left thigh | 92.1 |
|  | left ankle | 80.6 |
|  | right thigh | 93.6 |
|  | right ankle | 83.7 |
| Note - Patient B reported feeling a burning on her left side. She stated that her right leg felt cool, and that she felt a sensation as if a thumb were being pressed into the middle of the arch on her right foot. She reported that she had a stress fracture of the calchaneal bone on the right heel. | | |
| 50 minutes | left thigh | 91.9 |
|  | left ankle | 80.2 |
|  | right thigh | 93.6 |
|  | right ankle | 83.7 |
| Note - Patient B reported that she thought the doctor was touching her right foot, but he was not. | | |

TABLE F-continued

| TIME | LOCATION | TEMPERATURE (° F.) |
|---|---|---|
| 55 minutes | left thigh | 91.9 |
|  | left ankle | 80.1 |
|  | right thigh | 93.7 |
|  | right ankle | 83.3 |
| Note - Patient B reported that her left leg was feeling restless. | | |
| 60 minutes | left thigh | 92.7 |
|  | left ankle | 80.1 |
|  | right thigh | 93.9 |
|  | right ankle | 83.3 |
| 65 minutes | left thigh | 93.0 |
|  | left ankle | 80.1 |
|  | right thigh | 94.1 |
|  | right ankle | 83.3 |
| Note - Patient B rose at 66 minutes. | | |
| 70 minutes | left thigh | 91.0 |
|  | left ankle | 79.7 |
|  | right thigh | 91.0 |
|  | right ankle | 82.8 |

[A]Five minutes after first temperature reading in Table E.
The probes were removed after 70 minutes.

Example 4

Determination of Metabolic Activity

The topical medicament prepared in Example 1 was applied to the left inner forearm (below the elbow) of a patient. The treated area was then swabbed with a glass slide that was subsequently sandwiched between two ECG patches attached to leads to a Radio Shack digital, multi-meter. The initial reading (time=0) was 0.0 mV. Subsequent readings were taken at different intervals, and those results are reported in Table G.

TABLE G

| TIME (minutes after initial reading) | READING (mV) |
|---|---|
| 1 | 0.2 |
| 32 | 0.9 |
| 33 | 0.8 |
| 43 | 0.9 |
| 51 | 1.0 |
| 52 | 0.9 |
| 56 | 1.0 |
| 72 | 1.2 |
| 73 | 1.4 |
| 74 | 1.2 |
| 121 | 1.5 |

This test was carried out to show that oxygen activation from the compounded medicament occurs following the application to human skin with or without sweat.

This test was repeated using medicament that had been swabbed from another patient's back. However, the cream turned green in color and did not reproduce similar results with the ECG patches. It also took about 6 hours and 20 minutes for this person to notice the heat activation in the location where the medicament had been applied to the back.

Example 5

Metabolic Activity Comparison

Figure 1B:
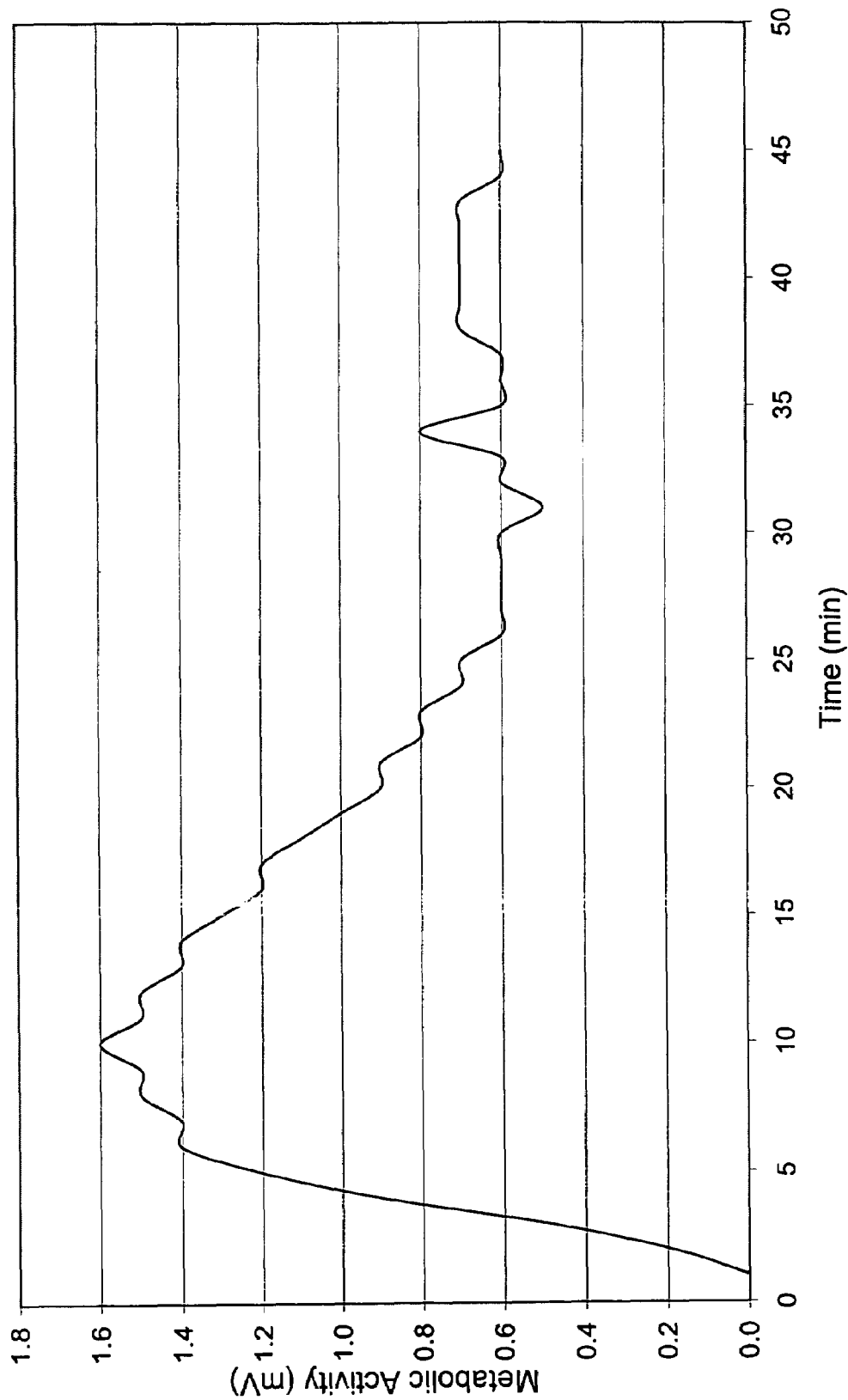
Figure 1C:
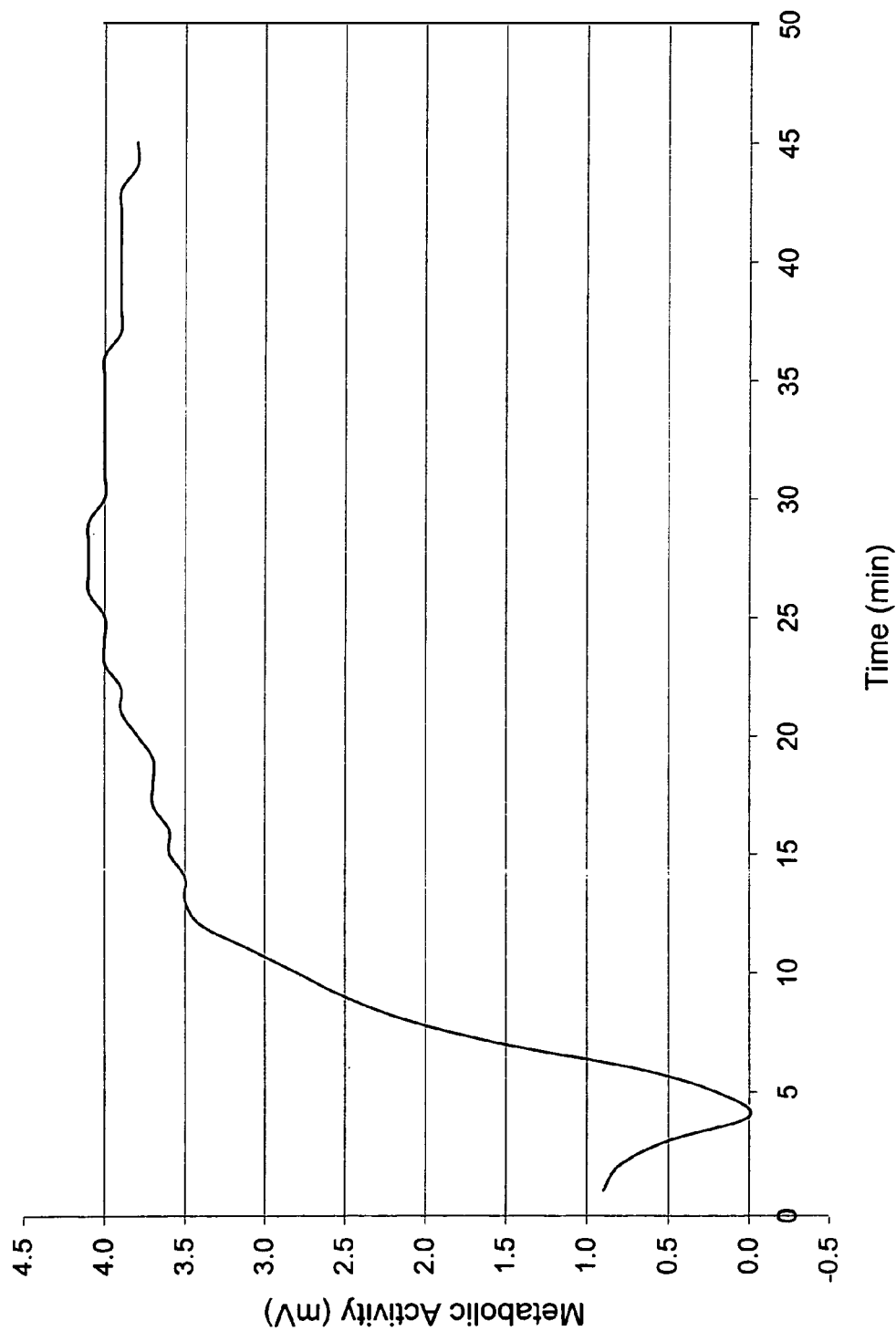
Figure 1D:
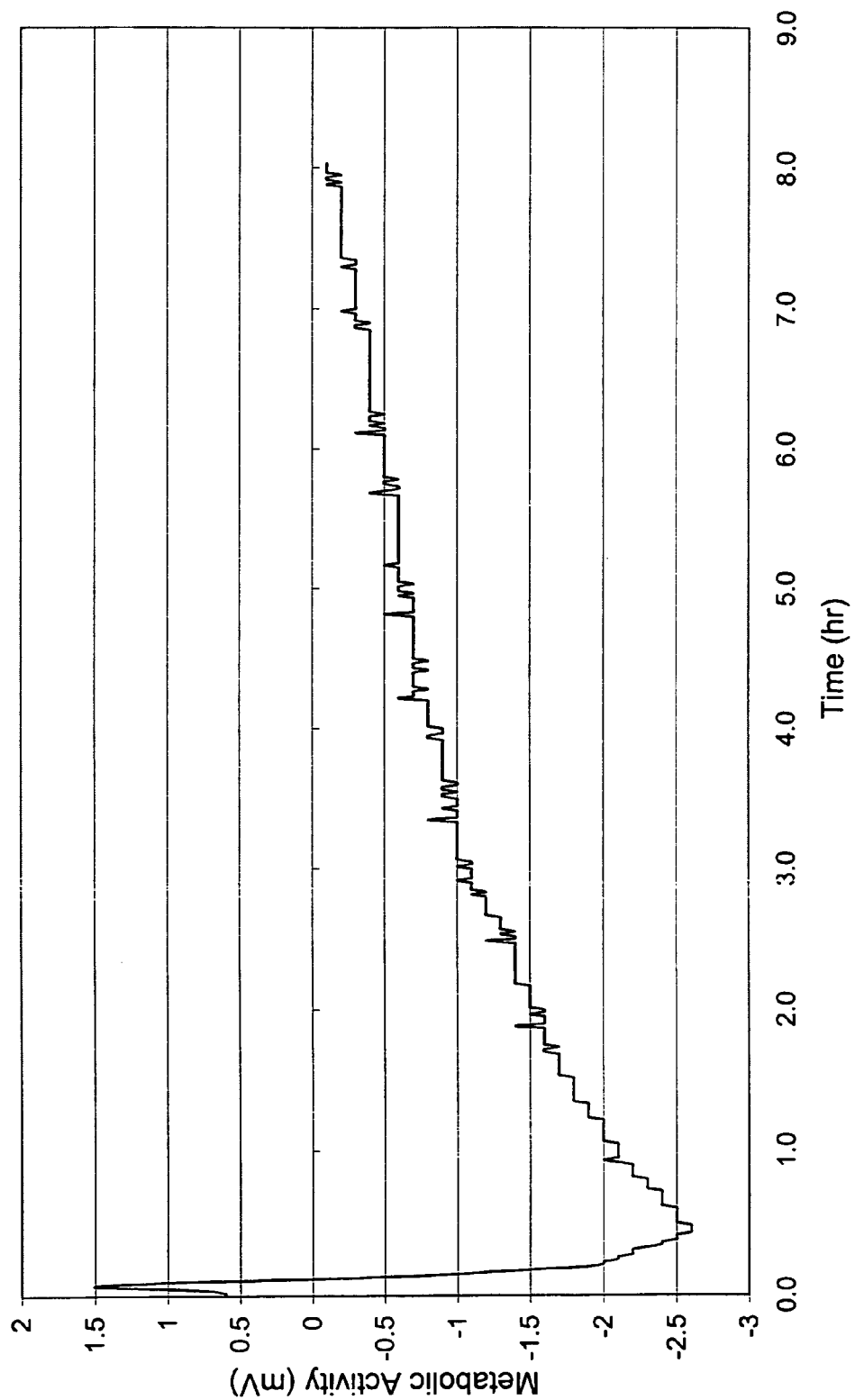

In this test, the metabolic activity of the topical medicament prepared in Example 1 was determined following the steps set forth in Example 4. The same steps were followed to determine the metabolic activity of two prior art products. FIG. 1a shows the metabolic activity of one prior art product (non-modified SOMBRA) over a 45-minute time period. FIG. 1b shows the metabolic activity of another prior art product (non-modified BIO-FREEZE) over a 45-minute time period. FIG. 1c shows the inventive medicament's metabolic activity over a 45-minute time period. A comparison of these figures shows that metabolic activity of the prior art peaks and then drops substantially over the 45-minute time period while the inventive medicament's metabolic activity maintains very high levels even after peaking. FIG. 1d shows the inventive medicament's metabolic activity over an 8-hour time period. This graph shows that this activity drops slowly over the 8-hour time period, thus providing prolonged treatment periods as compared to prior art products.

Example 6

Treatment of Patient with Inventive Topical Medicament

The patient in this example (hereinafter referred to as "Patient C") was a Caucasian female in her late 50s. Patient C was suffering from neuropathy in her feet, with symptoms including sharp, stabbing pains and contractures due to overstimulation of muscles. The condition had caused Patient C to take disability from work.

The topical medicament prepared in Example 1 was applied to Patient C's feet. Within 10 minutes, the contractures in her feet started to release, and she reported that her feet felt 90% better. Also, the sharp, stabbing pain was relieved for 6 hours after treatment.

I claim:

1. In a topical medicament comprising menthol and camphor, the improvement being that said medicament further comprises from about 0.02-0.5% by weight potassium and a source of oxygen present at sufficient levels to provide an oxygen level of from about 0.016-0.85% by weight, the percentages by weight being based upon the total weight of the medicament taken as 100% by weight.

2. The medicament of claim 1, wherein said medicament is in the form of a gel.

3. The medicament of claim 1, wherein said source of oxygen is selected from the group consisting of chlorites, spirulina, and mixtures of the foregoing.

4. The medicament of claim 3, wherein said source of oxygen is an alkali metal chlorite.

5. The medicament of claim 1, wherein said medicament comprises:
   at least about 0.5% by weight menthol and
   at least about 0.5% by weight camphor,
   based upon the total weight of the medicament taken as 1000% by weight.

6. The medicament of claim 1, wherein said medicament further comprises an ingredient selected from the group consisting of aloe vera extract, capsaicin, carbomer, decyl polyglucose, deionized water, grapefruit seed extract, green tea extract, orange peel extract, queen of the prairie extract, rose water, silica, sodium hydroxymethyl glycinate, vegetable glycerin, witch hazel, yucca extract, carbonates, bicarbonates, and mixtures of the foregoing.

7. The medicament of claim 1, wherein said medicament has a retained metabolic activity of at least about 20% over a 45-minute time period.

8. The medicament of claim 1, wherein said medicament has a retained metabolic activity of at least about 5% over an 8-hour time period.

* * * * *